United States Patent
Slaski

(10) Patent No.: US 10,639,208 B2
(45) Date of Patent: *May 5, 2020

(54) ELASTIC VENOUS COMPRESSION ORTHOSIS

(71) Applicant: LABORATOIRES INNOTHERA, Arcueil (FR)

(72) Inventor: Jean-Pierre Slaski, Brantigny (FR)

(73) Assignee: LABORATOIRES INNOTHERA, Arcueil (FR)

( * ) Notice: Subject to any disclaimer, the term of this patent is extended or adjusted under 35 U.S.C. 154(b) by 760 days.

This patent is subject to a terminal disclaimer.

(21) Appl. No.: 15/243,075

(22) Filed: Aug. 22, 2016

(65) Prior Publication Data

US 2017/0049631 A1 Feb. 23, 2017

(30) Foreign Application Priority Data

Aug. 20, 2015 (FR) ...................... 15 57839

(51) Int. Cl.
| | |
|---|---|
| A61F 13/08 | (2006.01) |
| D04B 1/26 | (2006.01) |
| A61F 5/01 | (2006.01) |
| D04B 1/18 | (2006.01) |

(52) U.S. Cl.
CPC ............ *A61F 13/08* (2013.01); *A61F 5/0111* (2013.01); *D04B 1/18* (2013.01); *D04B 1/265* (2013.01)

(58) Field of Classification Search
CPC ............ A61F 13/08; A61F 2013/00093; A61F 2013/00097; A61F 5/0109; A61F 5/0111; D04B 1/26; D04B 1/265

USPC .................................................. 602/60–63, 65
See application file for complete search history.

(56) References Cited

U.S. PATENT DOCUMENTS

| | | | |
|---|---|---|---|
| 2,680,960 A | 6/1954 | Hall | |
| 2010/0003436 A1* | 1/2010 | Lopez | ................. C08L 83/04 428/36.1 |
| 2015/0245951 A1* | 9/2015 | Convert | ................. A61F 13/08 66/178 A |
| 2017/0049633 A1* | 2/2017 | Slaski | ................. D04B 1/18 |

FOREIGN PATENT DOCUMENTS

| | | |
|---|---|---|
| DE | 202015101990 U1 | 5/2015 |
| FR | 2654925 A1 | 5/1991 |
| FR | 2852509 A1 | 9/2004 |
| GB | 790779 A | 2/1958 |

OTHER PUBLICATIONS

Jul. 13, 2016 Search Report issued in French Patent Application No. 1557839.

* cited by examiner

*Primary Examiner* — Keri J Nelson
(74) *Attorney, Agent, or Firm* — Oliff PLC

(57) ABSTRACT

An elastic venous compression orthosis has a top part and a leg part, the top part and the leg part having a top part knit thread and leg part knit thread, respectively, defining a network of knitted meshes, and a top part weft thread and leg part weft thread, respectively, the orthosis being characterized in that the top part has a reinforcement thread with an elongation at break, measured according to DIN 53834, of below 40% and a linear density of over 30 dTex.

20 Claims, 2 Drawing Sheets

ELASTIC VENOUS COMPRESSION ORTHOSIS

TECHNICAL FIELD

The present invention relates to an elastic venous retention and/or compression orthosis indicated in cases of vein disorders of a lower limb of a patient.

PRIOR ART

Elastic venous retention and/or compression orthoses, formerly known as "retention stockings (or hoses)" or "retention tights", are textile medical devices producing a therapeutic effect through retention and/or compression of the lower limbs, unlike "support stockings" (or even "support hoses" or "anti-fatigue stockings") and "fashion stockings", which are not medical devices with a therapeutic purpose.

The orthoses are designed to produce a therapeutic effect through retention and/or compression of the lower limb over a greater or lesser extent, usually with a pressure profile decreasing upwards from the ankle.

To permit strong compression of the lower limbs, the elastic venous compression orthoses are made from a knitted mesh with incorporation of an elastic weft thread, generally a covered elastane.

The orthosis is put onto the lower limb of the patient to be treated, as far as a position of use. The restoring force of the elastic fibres then exerts a compression.

The mesh and the threads, and the dimensioning of the rows of meshes, are chosen in such a way as to apply predetermined pressures at different altitudes of the lower limb, for example at the height of the ankle, at the start of the calf, at the level of the calf, at the popliteal fossa, etc., as far as the top of the thigh, said altitudes being conventionally designated B to G. These different pressures are defined for each class by reference to metrological jigs such as the leg model of French standard NF G 30-102 part B, annex B, corresponding to the "Hohenstein" leg model according to the German standard RAL-GZ 387, or as defined in the experimental European standard XP ENV 12718:2001.

Since the morphology of the lower limbs differs from one patient to another, an orthosis model is conventionally offered in several sizes in order to satisfy the target population. A size of a model is conventionally characterized by particular dimensions. The elasticity of the orthosis, however, allows one size to fit patients who have lower limbs of different dimensions. All the sizes of a model are referred to as a size "grid".

There is a constant need to improve the comfort of the orthoses.

An object of the invention is to meet this need at least in part.

SUMMARY OF THE INVENTION

According to the invention, this object is achieved by means of an orthosis having a top part, which is preferably ribbed, in French "bord-cote", hereafter "the top part", and a leg part, the top part and the leg part having a top part knit thread and a leg part knit thread, respectively, or "mesh thread" or "base thread", defining a network of knitted meshes, and a top part weft thread and leg part weft thread, respectively.

It is notable that the top part has a reinforcement thread, preferably different from the top part weft thread and the top part knit thread, and having an elongation at break, measured according to the standard DIN 53834, of below 40% and a linear density (i.e. linear mass density) of over 30 dTex.

Without being bound by this theory, the inventors have found that the presence of such a reinforcement thread very substantially improves the resistance to folds in the top part, and hence the comfort.

An orthosis according to the invention may also have one or more of the following optional and preferred features:
  the reinforcement thread is made of polyamide, preferably uncovered;
  the reinforcement thread has a linear density of over 40 dTex and/or below 60 dTex;
  the top part has an inner cuff and an outer cuff, folded back on the inner cuff, the reinforcement thread extending exclusively in the inner cuff;
  the top part weft thread has a covered core, preferably double-covered, preferably by means of an elastane covering thread, the core preferably being made of elastane;
  the leg part has a weft thread (called the "leg part weft thread") which is covered, preferably double-covered, the ratio of the linear density of the core of the leg part weft thread to the linear density of the core of the top part weft thread being greater than 1.9, preferably greater than 2.2;
  the linear density of the core of the top part weft thread is below 150 dTex and over 100 dTex;
  the top part knit thread is a single covered thread composed of an elastane core covered with a covering thread of polyamide;
the orthosis is an elastic venous compression orthosis of class I, II, III or IV, according to the ASQUAL system («Référentiel technique prescrit pour les orthèses élastiques de contention des membres», revision no 5, COFRAC). The invention also concerns the use of an orthosis according to the invention for treating a venous disease of lower limb of a patient.

BRIEF DESCRIPTION OF THE FIGURES

Other features and advantages of the invention will become clearer from reading the following detailed description and from examining the attached drawing, in which.

DEFINITIONS

Figures 1, 2:
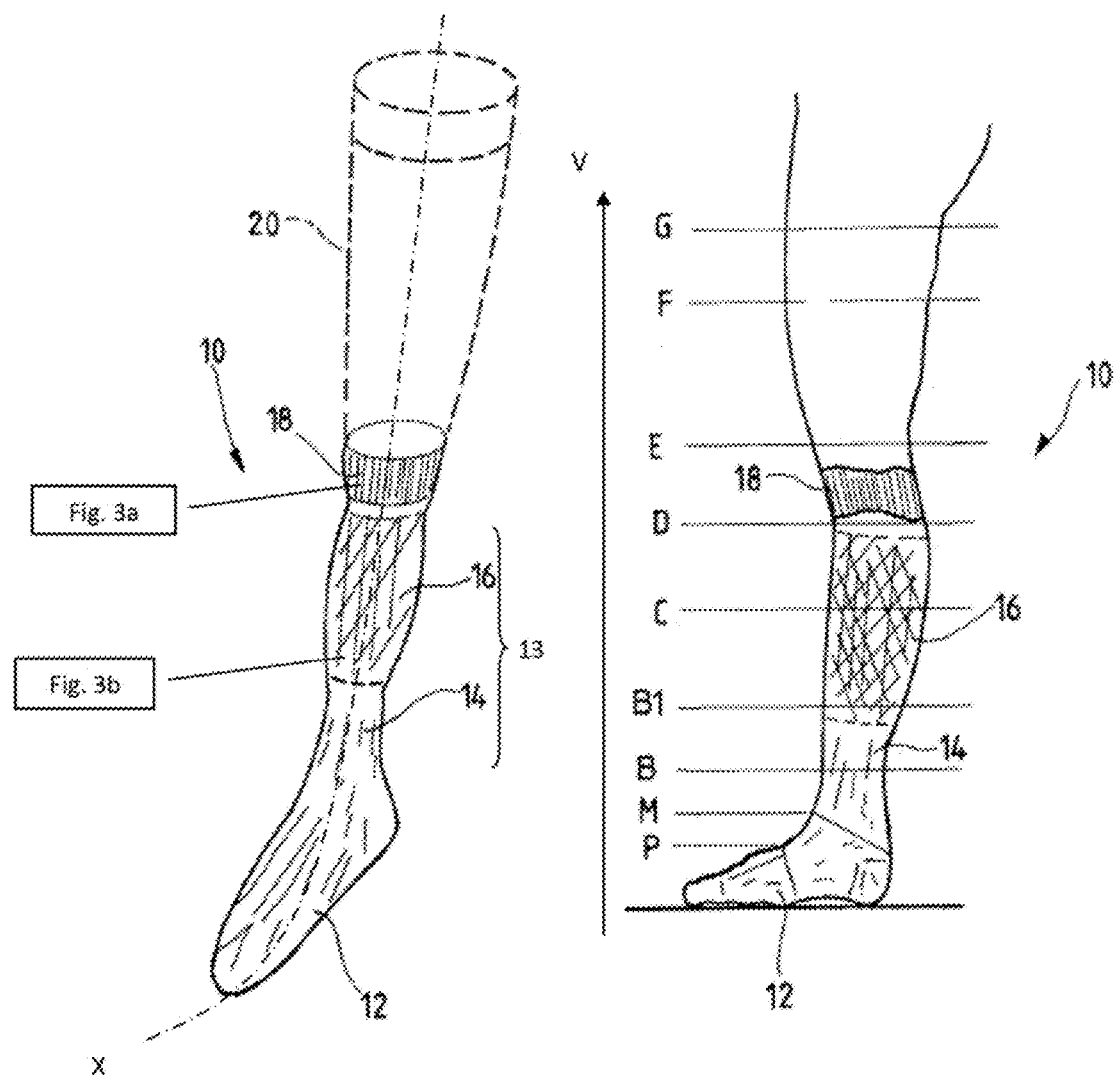
FIG. 1 is a schematic representation of an orthosis according to the invention.
FIG. 2 shows the orthosis from FIG. 1 fitted on a lower limb of a patient (position of use)

"Altitude" corresponds to a level in the vertical direction V when the orthosis is being worn by a patient standing straight and upright, as is shown in FIG. 2.

DETAILED DESCRIPTION

In FIGS. 1 and 2, reference sign 10 generally designates an orthosis 10 according to the invention.

The orthosis 10, having a general anatomical shape, comprises a foot part 12 enclosing the foot, a leg part 13 having an ankle part 14 enclosing the ankle and a calf part 16 enclosing the calf, and a knitted end part called the "top part" 18.

The orthosis 10 extends to a level situated below the knee, in the case where the orthosis is a "half-hose" (or "knee sock").

The configuration in the form of a sock is not limiting, and the orthosis 10 may also be produced in the form of a "thigh stocking", continued by a compressive thigh part 20. The orthosis 10 may also be produced in the form of tights and/or without a foot part 12 (stocking or tights of the "open foot" type).

The various adjoining parts of the orthosis 10 are preferably knitted continuously on a circular machine, according to conventional methods. The production of the orthosis 10 does not require any preparatory step for assembling the various parts, except for the operations of sewing on the foot part 12, if the latter is present.

In FIG. 2, the altitudes of the lower limb as defined by the morphological reference system indicated in the introduction (leg model or "Hohenstein jig") have been shown using standard notation:

B: ankle, at the point of its smallest circumference;
B1: junction between the Achilles tendon and the calf muscles;
C: calf, at the point of its greatest circumference;
D: just below the tibial tuberosity (that is to say just below the knee);
E: at the centre of the knee cap and above the back of the knee (that is to say at the level of the popliteal fossa);
F: at the middle of the thigh; and
G: at the top of the thigh.

The calf is the limb segment situated between levels B1 and D, and the ankle is the limb segment situated below level B1.

Figure 3A:
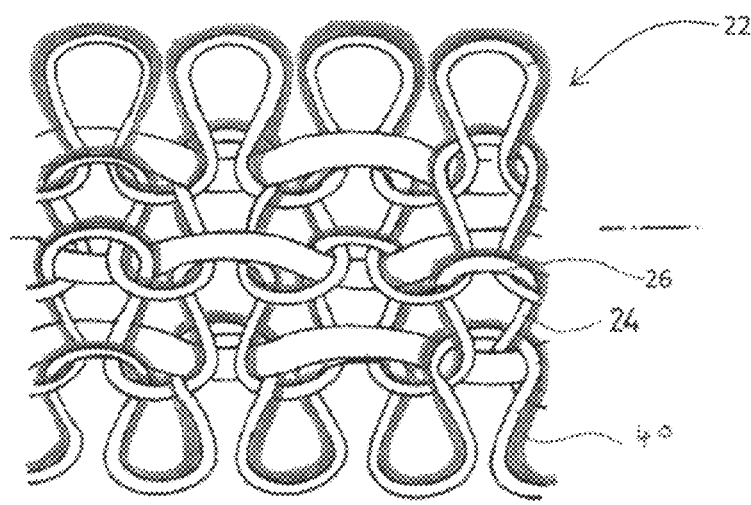
FIGS. 3a and 3b show a macroscopic view of the top part and of the leg part, respectively, of the orthosis from FIG. 1.
Figure 3B:
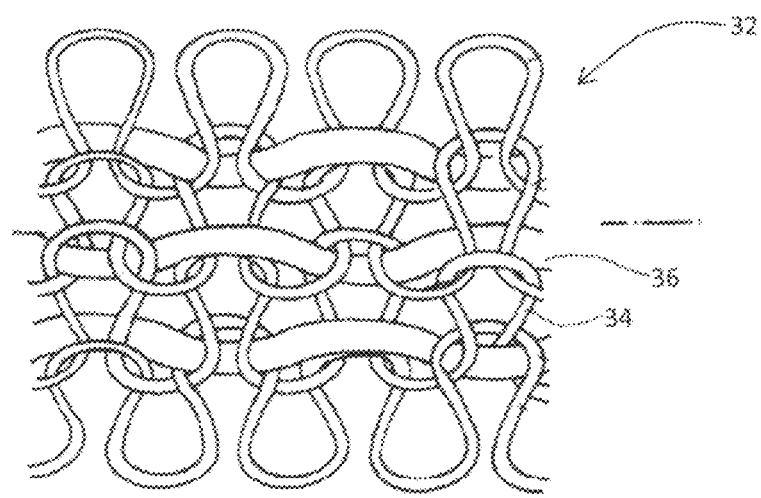

As is shown in FIG. 3, the top part 18 conventionally has a network of meshes 22 produced by means of a top part knit thread 24, a top part weft thread 26 being interlaced between said meshes.

The leg part 13 also conventionally has a network of meshes 32 produced by means of a leg part knit thread 34, a leg part weft thread 36 being interlaced between said meshes.

Figure 4:
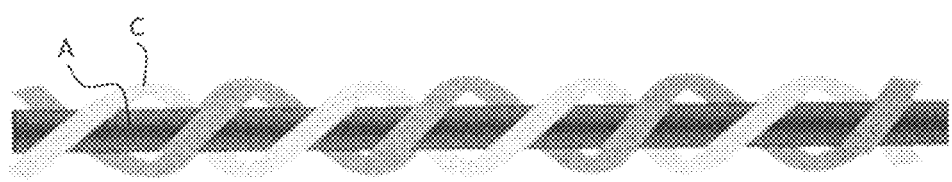
FIG. 4 is a schematic representation of a detail of a double-covered thread.

Preferably, the weft threads of the top part and of the leg part each have a core A, or "central thread", which is covered, preferably double-covered, by means of one or more covering threads C (see FIG. 4).

The nature of the threads and of the meshes is adapted depending on the desired action for the different parts of the orthosis, in particular depending on whether the action is to be one of retention or compression. This adaptation does not pose any particular difficulty to a person skilled in the art.

For an elastic venous compression orthosis, the pressure measured at the ankle may be 13 hPa or greater, 20 hPa or greater, or 30 hPa or greater, and/or less than 70 hPa, or less than 60 hPa.

In particular it may vary from 10 to over 36 mmHg (i.e. 13 to 48 hPa, although mmHg is commonly used as the unit of measurement of pressure in the field of phlebology and of medical compression).

Preferably, the pressure is decreasing, preferably continuously, in the portion from the ankle to the thigh, including the ankle and the thigh.

The elastic venous compression orthoses are divided into four textile classes according to the ASQUAL system, from class I (13 to 20 hPa≈10 to 15 mmHg at the ankle) to class IV (>48 hPa≈>36 mmHg at the ankle).

A weft thread conventionally extends transversely with respect to the principal axis X of the orthosis, shown in FIG. 1. More precisely, it extends orthoradially, spiralling about the principal axis of the orthosis and passing along the rows of meshes.

Top Part

Preferably, the top part 18 is a so-called "double cuff" structure, that is to say the result of the orthosis neck (which defines the opening through which the orthosis is put on) being folded over inwards or preferably outwards from the orthosis. It thus has an inner cuff $18_i$ intended to be in contact with the skin of the lower limb of the patient, and an outer cuff $18_e$ exposed to the outside and separated from the skin by the inner cuff.

In a preferred embodiment, the top part knit thread 24 is a single covered thread composed of an elastane core A covered with one or more covering threads C of polyamide (see FIG. 4).

Preferably, the linear density of the core of the top part knit thread 24 is below 45 dTex, preferably below 30 dTex, preferably below 25 dTex, preferably below 20 dTex, and/or above 10 dTex, preferably above 15 dTex.

Preferably, the linear density of the covering thread of the top part knit thread 24 is below 60 dTex, preferably below 50 dTex, preferably below 45 dTex, and/or above 20 dTex, preferably above 30 dTex, preferably above 40 dTex.

In one embodiment, the top part has only a single weft thread.

In a preferred embodiment, the top part weft thread 26 is a covered thread, preferably a double-covered thread.

Preferably, the difference between the elasticity of the material constituting the core A (see FIG. 4) of the top part weft thread and the elasticity of the material constituting the one or more covering threads C of the top part weft thread is less than 10%, 5%, 2% or 1% of the elasticity of the material constituting the core of the weft thread of the top part. Preferably, the materials constituting the core and the covering thread of the top part weft thread 26 are identical.

Preferably, the top part weft thread 26 is composed of a core of elastane covered, preferably double-covered, with an elastane covering thread. The double covering of elastane facilitates the knitting of the orthosis.

Surprisingly, without being able to explain this theoretically, the inventors have in particular discovered that the orthosis may be easily produced using standard knitting machines. The investments and the running costs are advantageously limited as a result.

Without being bound by this theory, the inventors consider that the elasticity of the covering thread prevents the covering thread from limiting the capacities of elastic deformation of the weft thread.

Advantageously, a top part weft thread 26 composed of an elastane core double-covered with an elastane covering thread may be used like the conventional weft threads, without a specific unwinding system, in contrast in particular to simple threads of elastane.

Preferably, the linear density of the core of the top part weft thread 26 is below 150 dTex, preferably below 140 dTex, preferably below 135 dTex, and/or above 100 dTex, preferably above 110 dTex, preferably above 120 dTex, preferably above 125 dTex.

Preferably, the linear density of the covering thread of the top part weft thread 26 is below 40 dTex, preferably below 30 dTex, preferably below 25 dTex, and/or above 10 dTex, preferably above 15 dTex, preferably above 20 dTex.

According to a preferred embodiment of the invention, the top part moreover has a reinforcement thread 40, which is different from the weft thread and from the knit thread and which extends transversely, like the weft thread.

In one embodiment, the top part has only a single reinforcement thread.

Preferably, the reinforcement thread does not extend over a thigh part and/or an ankle part and/or a calf part and/or a foot part that are intended to enclose a thigh, an ankle, a calf and a foot, respectively, of a patient wearing the orthosis.

Preferably, the reinforcement thread extends exclusively in the top part, preferably over more than 90%, preferably over substantially 100% of the height of the top part. Advantageously, the presence of the reinforcement thread in the top part alone does not modify the behaviour, in particular the elasticity, of the parts of the orthosis that extend below the top part.

Preferably, the reinforcement thread 40 only extends in the inner cuff 18$_i$ of the top part. Comfort is thereby improved.

Preferably, the reinforcement thread 40 has an elongation at break of below 40%, preferably of below 35%, preferably of below 30%, preferably of below 28%, preferably of below 27%.

The reinforcement thread 40 may have an elongation at break of over 10%, over 20%, or even over 25%.

The elongation at break may be measured according to the standard DIN 53834.

The reinforcement thread 40 is preferably of polyamide. Preferably, the reinforcement thread 40 is a "simple" thread, i.e. not covered.

It preferably has a linear density of over 30 dTex, preferably of over 35 dTex, preferably of over 40 dTex and/or below 60 dTex, preferably below 50 dTex, more preferably below 45 dTex.

The reinforcement thread is preferably different from the top part weft thread and preferably different from the knit thread. In one embodiment, two knit threads may be used simultaneously to knit the top part. In particular, a first knit thread may be unrolled from a first knitting feed, and a second knit thread may be unrolled from a second feed. One of the first and second knit threads may constitute the reinforcement thread.

The reinforcement thread may also be formed by a local reinforcement of the knit thread and/or of the weft thread. For example, the knit thread may be locally reinforced, for example coated periodically with a liner, in such a way that it has, in the one or more reinforced regions, an elongation at break of below 40%, measured according to DIN 53834, and a linear density of over 30 dTex.

The reinforcement thread may extend transversely, like the weft thread, or may preferably define meanders, like a knit thread. In particular, the reinforcement thread may be knitted in parallel with the knit thread.

In one embodiment, the reinforcement thread is added to the network of meshes formed by the weft thread and the knit thread. In other words, the knit is not destructured, that is to say does not break up in several pieces, if the reinforcement thread is removed.

Preferably, the reinforcement thread is coiled, preferably in spiral, over 10 rounds, over 50 rounds, over 100 rounds around the principal axis of the top part (axis of the top part in the position of use, referenced X in FIG. 1).

In one embodiment, the portion of the top part reinforced by the reinforcement thread is spaced more than 2 mm, 5 mm, 10 mm, or even 15 mm from the upper edge of the top part, which delimits the opening by which the orthosis is slipped onto the patient's limb.

Leg Part

The leg part knit thread may be identical or different depending on the portion of the leg part in question. In particular, it may be different in the ankle part 14 and calf part 16.

The knit thread may be identical in the calf part 16 and thigh part 20, and/or in the ankle part 14 and thigh part 20.

In one embodiment, the leg part has only a single knit thread.

In a preferred embodiment, the leg part knit thread 34 is a single covered thread composed of an elastane core covered with one or more covering threads of polyamide.

Preferably, the linear density of the core of the leg part knit thread 34 is below 45 dTex, preferably below 30 dTex, preferably below 25 dTex, preferably below 20 dTex, and/or over 10 dTex, preferably over 15 dTex.

Preferably, the linear density of the covering thread of the leg part knit thread 34 is below 60 dTex, preferably below 50 dTex, preferably below 45 dTex, and/or over 20 dTex, preferably over 30 dTex, preferably over 40 dTex.

In one embodiment, the leg part has only a single weft thread.

In a preferred embodiment, the leg part weft thread 36 is a double covered thread composed of an elastane core covered with a covering thread of polyamide. Advantageously, such a covering thread makes the orthosis easier to put on.

Preferably, the core of the top part weft thread has a linear density of less than 0.7 times that of the core of the weft thread of the leg part.

Preferably, the ratio of the linear density of the core of the leg part weft thread 36 to the linear density of the core of the top part weft thread 26 is over 1.9, preferably over 2.0, preferably over 2.1, preferably over 2.2, preferably over 2.3, and/or below 3.0, preferably below 2.8, preferably below 2.6, preferably below 2.5, preferably below 2.4.

Preferably, the linear density of the core of the leg part weft thread 36 is below 350 dTex, preferably below 340 dTex, and/or over 250 dTex, preferably over 280 dTex, preferably over 290 dTex, preferably over 300 dTex, preferably over 320 dTex.

Preferably, the linear density of the covering thread of the leg part weft thread 36 is below 40 dTex, preferably below 30 dTex, preferably below 25 dTex, and/or over 10 dTex, preferably over 15 dTex, preferably over 20 dTex.

In a preferred embodiment, the leg part has no reinforcement thread, like the top part.

Of course, the invention is not limited to the embodiments described and shown, which are provided for illustrative purposes only.

The invention claimed is:

1. Elastic venous retention and/or compression orthosis indicated in case of venous disease of the lower limb of a patient, said orthosis having a top part and a leg part, said leg part having an ankle part configured to wrap the ankle of the limb and a calf part configured to wrap the calf of the limb, the top part and the leg part having a top part knit thread and leg part knit thread, respectively, defining a network of knitted meshes, and a top part weft thread and leg part weft thread, respectively, wherein the top part has a reinforcement thread with an elongation at break, measured according to the standard DIN 53834, of below 40% and a linear density of over 30 dTex.

2. Orthosis according to claim 1, the reinforcement thread having an elongation at break of below 30%.

3. Orthosis according to claim 1, the reinforcement thread being made of polyamide.

4. Orthosis according to claim 1, the reinforcement thread having a linear density of over 40 dTex.

5. Orthosis according to claim 1, the reinforcement thread having a linear density of below 60 dTex.

6. Orthosis according to claim 1, the top part having an inner cuff and an outer cuff folded back on the inner cuff, the reinforcement thread extending exclusively in the inner cuff.

7. Orthosis according to claim 1, the top part weft thread having an elastane core double-covered by means of a covering thread of elastane.

8. Orthosis according to claim 7, the linear density of the core of the top part weft thread being below 150 dTex and over 100 dTex.

9. Orthosis according to claim 1, said leg part weft thread and said top part weft thread each having a core and being covered, the ratio of the linear density of the core of the leg part weft thread to the linear density of the core of the top part weft thread being greater than 1.9.

10. Orthosis according to claim 9, said ratio being greater than 2.2.

11. Orthosis according to claim 1, the top part knit thread being a single covered thread composed of an elastane core covered with a covering thread of polyamide.

12. Orthosis according to claim 1, of class I, II, III or IV, according to the ASQUAL system.

13. Orthosis according to claim 1, comprising a single reinforcement thread.

14. Orthosis according to claim 1, wherein the reinforcement thread extends transversely, as the weft thread, or is knitted in parallel with the knit thread.

15. Orthosis according to claim 1, wherein the reinforcement thread is different from the top part weft thread.

16. Orthosis according to claim 1, wherein the ankle part is configured to apply pressure measured at the ankle between 13 and 48 hPa.

17. Orthosis according to claim 1, wherein the reinforcement thread extends exclusively in the top part, over 90%, of the height of the top part.

18. Elastic venous retention and/or compression orthosis indicated in case of venous disease of the lower limb of a patient, said orthosis having a top part and a leg part, said leg part having an ankle part configured to wrap the ankle of the limb and a calf part configured to wrap the calf of the limb,
the top part and the leg part having a top part knit thread and leg part knit thread, respectively, defining a network of knitted meshes, and a top part weft thread and leg part weft thread, respectively,
wherein the reinforcement thread being coiled over 10 rounds around the principal axis of the top part.

19. Elastic venous retention and/or compression orthosis indicated in case of venous disease of the lower limb of a patient, said orthosis having a top part and a leg part, said leg part having an ankle part configured to wrap the ankle of the limb and a calf part configured to wrap the calf of the limb,
the top part and the leg part having a top part knit thread and leg part knit thread, respectively, defining a network of knitted meshes, and a top part weft thread and leg part weft thread, respectively,
wherein the top part has a reinforcement thread with an elongation at break, measured according to the standard DIN 53834, of below 40% and a linear density of over 30 dTex, and
wherein the reinforcement thread extends exclusively in the top part.

20. Elastic venous retention and/or compression orthosis according to claim 19, wherein the reinforcement thread extends over 90% of the height of the top part.

* * * * *